US008150536B2

(12) United States Patent
Osypka

(10) Patent No.: US 8,150,536 B2
(45) Date of Patent: Apr. 3, 2012

(54) LOW PROFILE ACTIVE FIXATION CARDIAC LEAD HAVING TORQUE TRANSMITTING MEANS

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 139 days.

(21) Appl. No.: 11/811,376

(22) Filed: Jun. 8, 2007

(65) Prior Publication Data
US 2007/0299493 A1  Dec. 27, 2007

Related U.S. Application Data

(60) Provisional application No. 60/812,758, filed on Jun. 12, 2006.

(51) Int. Cl.
*A61N 1/05* (2006.01)
(52) U.S. Cl. ........................................ 607/127; 607/126
(58) Field of Classification Search .................. 607/116, 607/120, 122, 126–127; 600/374
See application file for complete search history.

(56) References Cited

U.S. PATENT DOCUMENTS

| | | | | |
|---|---|---|---|---|
| 4,924,881 A * | 5/1990 | Brewer | ......................... | 607/127 |
| 5,020,545 A * | 6/1991 | Soukup | ......................... | 607/127 |
| 5,676,694 A * | 10/1997 | Boser et al. | .................... | 607/122 |
| 6,108,582 A * | 8/2000 | Fischer, Sr. | .................... | 607/127 |
| 6,129,750 A * | 10/2000 | Tockman et al. | ............. | 607/125 |
| 6,129,751 A * | 10/2000 | Lucchesi et al. | ............... | 607/127 |
| 6,214,002 B1 * | 4/2001 | Fleischman et al. | ............ | 606/41 |
| 6,289,251 B1 * | 9/2001 | Huepenbecker et al. | ..... | 607/122 |
| 6,909,920 B2 * | 6/2005 | Lokhoff et al. | ............... | 607/127 |
| 7,313,445 B2 * | 12/2007 | McVenes et al. | ............. | 607/127 |
| 2002/0123785 A1 * | 9/2002 | Zhang et al. | .................... | 607/126 |
| 2002/0147484 A1 * | 10/2002 | Dahl et al. | .................... | 607/116 |
| 2004/0014355 A1 * | 1/2004 | Osypka et al. | ................ | 439/502 |
| 2004/0054389 A1 * | 3/2004 | Osypka | ........................ | 607/120 |
| 2004/0064172 A1 * | 4/2004 | McVenes et al. | ............. | 607/122 |
| 2004/0127967 A1 * | 7/2004 | Osypka | ........................ | 607/122 |
| 2006/0122682 A1 * | 6/2006 | Sommer et al. | ............... | 607/127 |

* cited by examiner

*Primary Examiner* — Carl H Layno
*Assistant Examiner* — Paula J Stice
(74) *Attorney, Agent, or Firm* — Scott D. Wofsy; Edwards Wildman Palmer LLP

(57) ABSTRACT

An active fixation cardiac lead is disclosed that includes an elongated lead body having opposed proximal and distal end portions and an interior lumen that extends therethrough. A rotatable fixation element is operatively associated with the distal end portion of the lead body and a tubular torque-transmitting member extends through the interior lumen of the lead body. The tubular torque-transmitting member has a distal end connected to the fixation element and a proximal end connected to a rotatable actuator operatively associated with the proximal end portion of the lead body. Preferably, the rotatable actuator is part of a connector assembly that is operatively associated with the proximal end portion of the lead body.

20 Claims, 3 Drawing Sheets

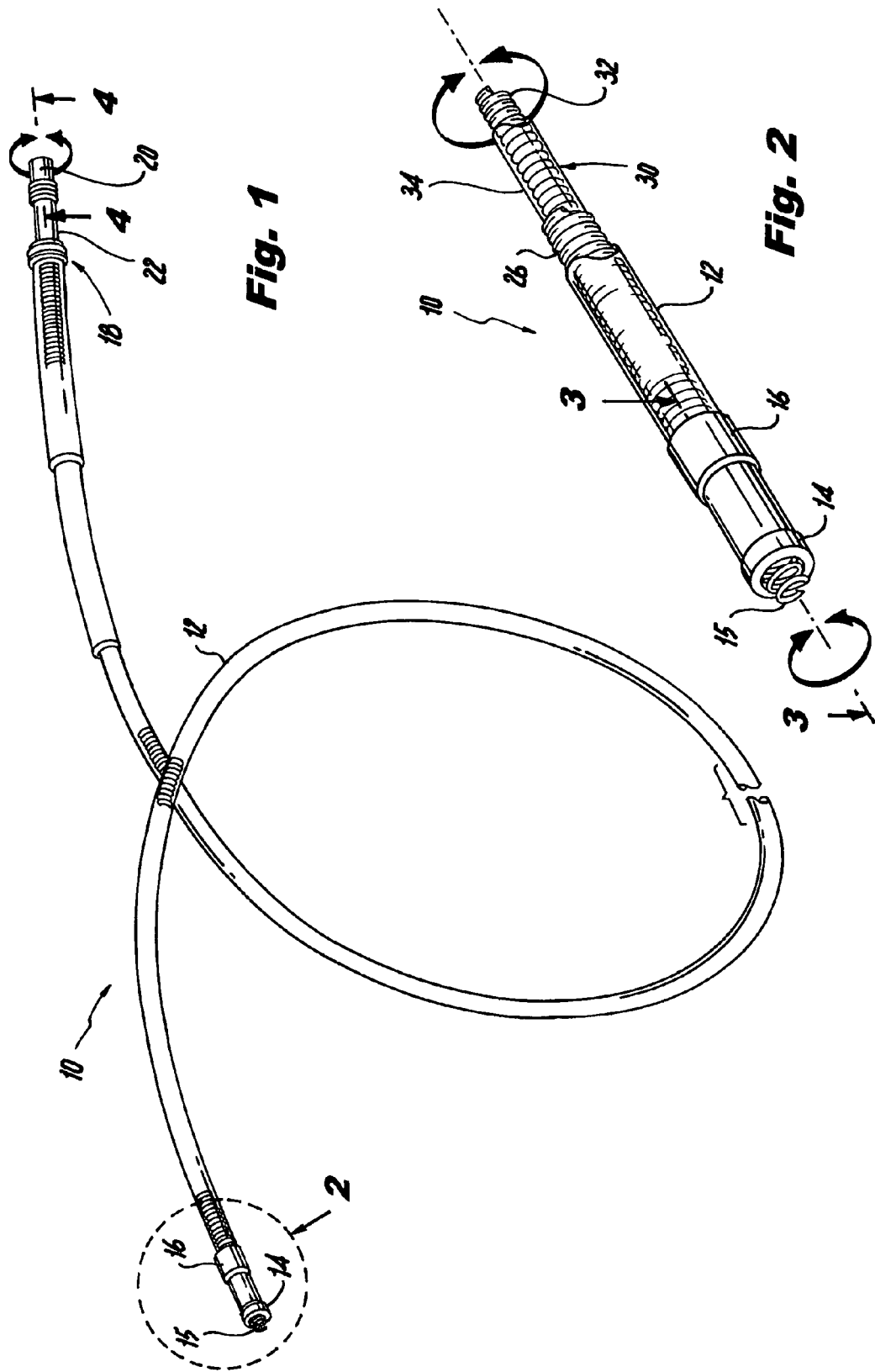

LOW PROFILE ACTIVE FIXATION CARDIAC LEAD HAVING TORQUE TRANSMITTING MEANS

CROSS-REFERENCE TO RELATED APPLICATION

The subject application claims the benefit of priority to U.S. Provisional Patent Application Ser. No. 60/812,758 filed Jun. 12, 2006, the disclosure of which is incorporated herein by reference in its entirety.

BACKGROUND OF THE INVENTION

1. Field of the Invention

The subject invention is directed to cardiac leads, and more particularly, to a low profile active fixation cardiac pacing lead having a torque transmitting mechanism for activating the fixation helix at the distal end of the lead.

2. Description of Related Art

Current active fixation leads are designed with an extendable and retractable fixation helix or screw, that can be retracted for transvenous insertion of the lead into the right atrium and ventricle and then extended so that the lead can be actively screwed into the endocardial wall.

Direct drive leads in which the fixation screw can be extended/retracted by a stylet shaped with a screwdriver tip are known. It is also known to connect the connector pin of the lead connector (e.g., IS-1 connector) to the fixation screw by way of the inner conductor coil. The direct drive mechanism has some advantages in that a straight or preformed J-shaped stylet can be introduced at the same time the helix is extended or retracted. The conductor coil drive mechanism is disadvantageous in that there is a delay in the transmission of torque from the connector pin to the helix.

In addition, the coil driven type requires a coaxial lead body design as compared to an inline lead body, since the inner conductor coil has to be turned relative to the outer connector coil. Such a design tends to increase the overall cross-sectional profile of the lead body. The subject invention overcomes the disadvantages associated with the drive mechanism in prior art active fixation leads.

SUMMARY OF THE INVENTION

The subject invention is directed to a new and useful cardiac pacing lead that includes, among other things, an elongated lead body having opposed proximal and distal end portions and an interior lumen that extends therethrough. A rotatable fixation element in the form of a helical fixation screw is operatively associated with the distal end portion of the lead body and a tubular torque-transmitting member extends through the interior lumen of the lead body.

The tubular torque-transmitting member has a distal end connected to the fixation element and a proximal end connected to a rotatable actuator operatively associated with the proximal end portion of the lead body. Preferably, the rotatable actuator is part of a connector assembly (e.g., an IS-1 type connector assembly) that is operatively associated with the proximal end portion of the lead body.

In one embodiment of the subject invention, the torque-transmitting member includes an electrically inactive helically wound coil that is preferably covered by a polymer tube. Preferably, the polymer tube is heat shrunk over the helically wound coil. In another embodiment of the subject invention, the torque-transmitting member includes an electrically inactive braided structure that is either covered by a heat shrunk polymer tube or embedded within a polymer tube.

An electrode assembly is operatively associated with the distal end portion of the lead body. The electrode assembly is operatively connected to the connector assembly by way of a conductor coil that extends through the interior lumen of the lead body. Preferably, the conductor coil is in the form of a multifilar conductor coil. The electrode assembly is preferably configured as a bipolar pacing assembly and includes a distal tip electrode and a proximally spaced apart ring electrode. It is envisioned however, that the electrode assembly could be configured as a unipolar pacing assembly and so as to only include a distal tip electrode.

The subject invention is further directed to a cardiac lead that includes an elongated flexible lead body having opposed proximal and distal end portions and an interior lumen that extends therethrough. An electrode assembly and a helical fixation screw are operatively associated with the distal end portion of the lead body and a connector assembly is operatively associated with the proximal end portion of the lead body. The connector assembly includes a rotatable actuator.

A conductor coil extends through the interior lumen of the lead body between the electrode assembly and the connector assembly, and a tubular torque-transmitting member extends coaxially through the conductor coil. A distal end of the torque-transmitting member is connected to the helical fixation screw and a proximal end of the torque-transmitting member is connected to the rotatable actuator of the connector assembly. This construction allows for a relatively low profile lead body design and a 1:1 torque ration between the proximal actuation and distal fixation screw.

These and other features of the low profile active fixation cardiac pacing lead of the subject invention will become more readily apparent to those skilled in the art from the following detailed description of the preferred embodiment taken in conjunction with the drawings.

BRIEF DESCRIPTION OF THE DRAWINGS

So that those skilled in the art to which the subject invention appertains will readily understand how to make and use the active fixation cardiac pacing leads of the subject invention without undue experimentation, preferred embodiments thereof will be described in detail hereinbelow with reference to certain figures, wherein:

FIG. 1 is a perspective view of a low profile active fixation cardiac pacing lead constructed in accordance with a preferred embodiment of the subject invention;

FIG. 2 is an enlarged localized perspective view of the distal end portion of the cardiac pacing lead of FIG. 1, with the outer sheath and multifilar conductor coil cut away to show the torque-transmitting member of the subject invention;

DETAILED DESCRIPTION OF PREFERRED EMBODIMENTS

Figure 3:
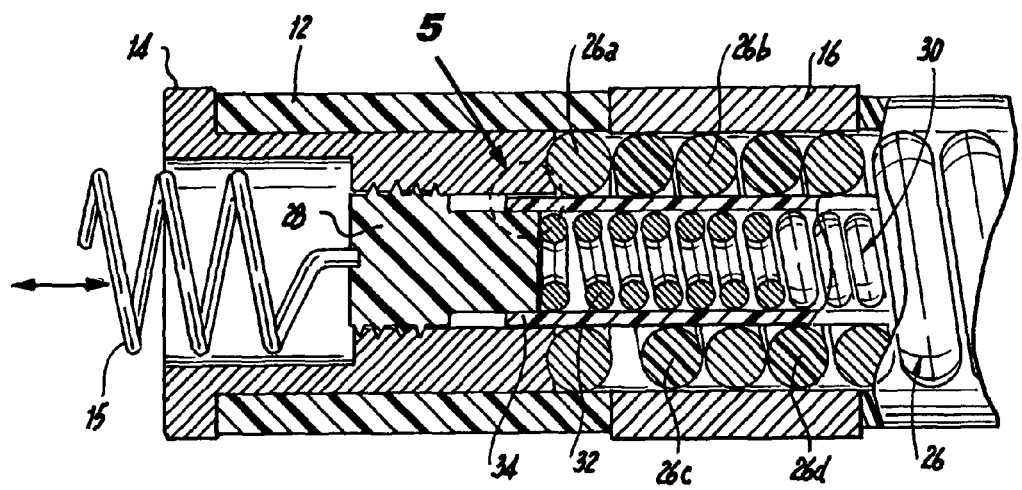
FIG. 3 is a cross-sectional view of the distal end portion of the cardiac lead of the subject invention, taken along line 3-3 of FIG. 2, illustrating the engagement of the torque-transmitting member and the helical fixation screw, wherein the torque-transmitting member comprises an electrically inactive helically wound coil covered or otherwise coated by a polymer tube.

Referring now to the drawings wherein like reference numerals identify similar structural features or elements of the medical devices disclosed herein, there is illustrated in FIG. 1 a bipolar low profile active fixation cardiac pacing lead constructed in accordance with a preferred embodiment of the subject invention and designated generally by reference numeral 10. Bipolar active fixation leads of this type are disclosed for example in U.S. Pat. No. 7,187,980 to Osypka et al., the disclosure of which is herein incorporated by reference in its entirety.

As is typical, bipolar active fixation lead 10 includes a helical fixation screw 15 that is adapted and configured to actively secure the distal tip of pacing lead 10 to the endocardial wall. As discussed in more detail below, the tubular torque transmitting assembly of the subject invention is configured to effectuate rotation and installation of fixation screw 15. More particularly, using the torque transmitting mechanism of the subject invention, fixation screw 15 can be retracted for transvenous insertion of the lead into the right atrium or ventricle and then extended so that the lead can be actively screwed into the endocardial wall.

Referring to FIG. 1, cardiac pacing lead 10 includes an elongated flexible body 12 having opposed proximal and distal end portions. The flexible lead body 12 is preferably formed of a durable biocompatible elastomeric material, such as, for example, silicone or a similar biocompatible material. Pacing lead 10 has a tip electrode 14 at the distal end thereof and a ring electrode 16 spaced proximally from tip electrode 14 to facilitate bipolar pacing/sensing. The electrodes 14, 16 are preferably coated with or otherwise formed from a medical grade stainless steel, a platinum-iridium alloy or a similar biocompatible metallic material.

A connector 18 is operatively associated with the proximal end portion of lead body 12 for interfacing with a cardiac rhythm management device such as for example a pacemaker or defibrillator. The connector 18 can be in the form of an IS-1 type connector, an LV-1 type connector, an IS-4 type connector or another type of standardized connector known in the art. Importantly, the connector 18 is constructed with relatively rotatable pin and ring elements 20, 22. The distal rotatable pin element 20 is operatively associated with and controls the torque-transmitting member 30 of the subject invention, shown for example in FIG. 2, and explained in further detail below with respect to FIG. 4.

With continuing reference to FIGS. 1 and 2, a multifilar conductor coil 26 extends through the interior lumen of lead body 12 from the connector 18 to the tip and ring electrodes 14, 16 associated with the distal end portion of lead body 12. The multifilar conductor coil 26 can be configured in a conventional manner with between four and six filars or filaments, or it can be constructed in accordance with the principles and advantages set forth in U.S. Pat. No. 6,978,185 to Osypka or U.S. Pat. No. 7,158,837 to Osypka et al., the disclosure of which are herein incorporated by reference in their entireties. In such an instance, the multifilar conductor coil 26 would be formed from a series of helically wound active and inactive filars, providing electrical isolation, low impedance and system redundancy.

Figure 4:
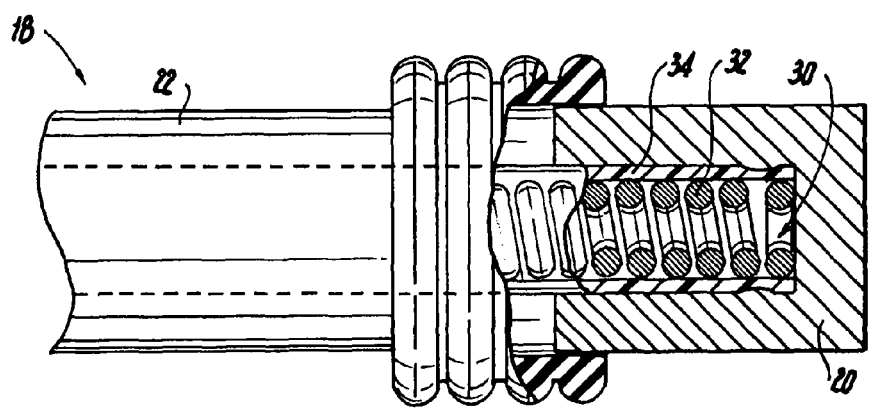
FIG. 4 is a cross-sectional view of the proximal end portion of the cardiac lead of the subject invention, taken along line 4-4 of FIG. 1, illustrating the engagement of the torque-transmitting member and the rotatable pin portion of the proximal connector.

Referring to FIG. 3, the multifilar conductor coil 26 includes at least one active filar 26a that is operatively associated with tip electrode 14 and at least one active filar 26b that is operatively associated with the ring electrode 16. Inactive filars 26c, 26d are co-wound with the active filars 26a, 26b, to electrically isolate the active filars 26a, 26b from one another. Those skilled in the art will readily appreciate that the wiring arrangement shown in FIG. 4 is merely exemplary. Alternative wiring arrangements utilizing a multifilar conductor coil are also envisioned.

As noted above, pacing lead 10 includes a distal fixation helix or screw 15 adapted and configured to actively secure the distal tip of pacing lead 10 to the endocardial wall. As best seen in FIG. 3, the fixation helix 15 is electrically inactive, in that the threaded plug 28 with which it is associated is formed from a non-conductive material, such as plastic or a self-lubricating polymeric material such as PTFE. However, it is envisioned that the fixation helix 15 can be electrically active to perform pacing or sensing tasks. In such an instance, a conductive path would be provided between the electrically active tip electrode 14 and the fixation helix 15. One way to achieve this would be to form the threaded plug 28 from a conductive material. Those skilled in the art will readily appreciate that this can also be achieved by other known means without undue experimentation.

Referring now to FIGS. 1 through 4, in accordance with the subject invention, the fixation helix 15 is screwed into place or otherwise axially rotated by way of a torque-transmitting member or torquing tube 30 that extends through the interior lumen of the multifilar conductor coil 26. Torque-transmitting member 30 includes an electrically inactive helically wound coil 32 that is covered by or otherwise coated with polymer tubing 34. Tubing 34 is preferably heat shrunk (e.g., heat reflow process) over the coil 32. This process connects the wound filars of the electrically inactive coil 32 together and allows for a 1:1 torque ratio from the proximal end of the lead body 12 to the distal end of the lead body, while keeping the necessary flexibility of the lead body 12.

Figure 5:
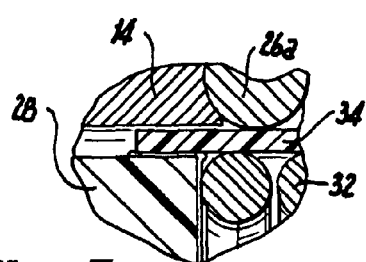
FIG. 5 is a localized view of the site of a joined connection between the torque-transmitting member and the helical fixation screw.
Figure 6:
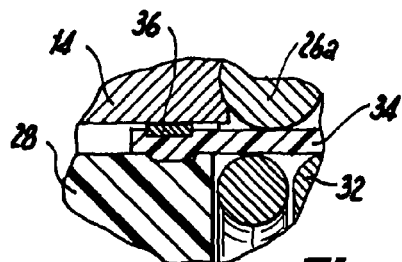
FIG. 6 is a localized view of the site of a clipped connection between the torque-transmitting member and the helical fixation screw.

As best seen in FIG. 3, the distal end of the torque-transmitting member 30 is operatively connected to the threaded plug 28 associated with the fixation helix 15. It is envisioned that the distal end of torque-transmitting member 30 can be connected to the threaded plug 28 or otherwise connected directly to the proximal end of fixation screw 15, or to another intermediate connective structure by laser welding, crimping or a similar joining technique including, but not limited to gluing, as shown for example in FIG. 5. It is also envisioned that torquing tube 30 could be connected to plug 28 or directly to fixation screw 15 by a mechanical clip 36 or the like, as shown for example in FIG. 6.

Referring to FIG. 4, the proximal end of the torque transmitting member 30 is operatively connected to the rotateable pin portion 20 of connector 18 (or to another rotateable portion of the connector) by laser welding, crimping or a similar joining technique. In operation, to secure fixation screw 15 into the endocardial wall, rotation of pin portion 20 will cause axial rotation of the torque-transmitting member 30 and corresponding rotation of the threaded plug 28 and together with the helical fixation screw 15 carried thereby.

Figure 7:
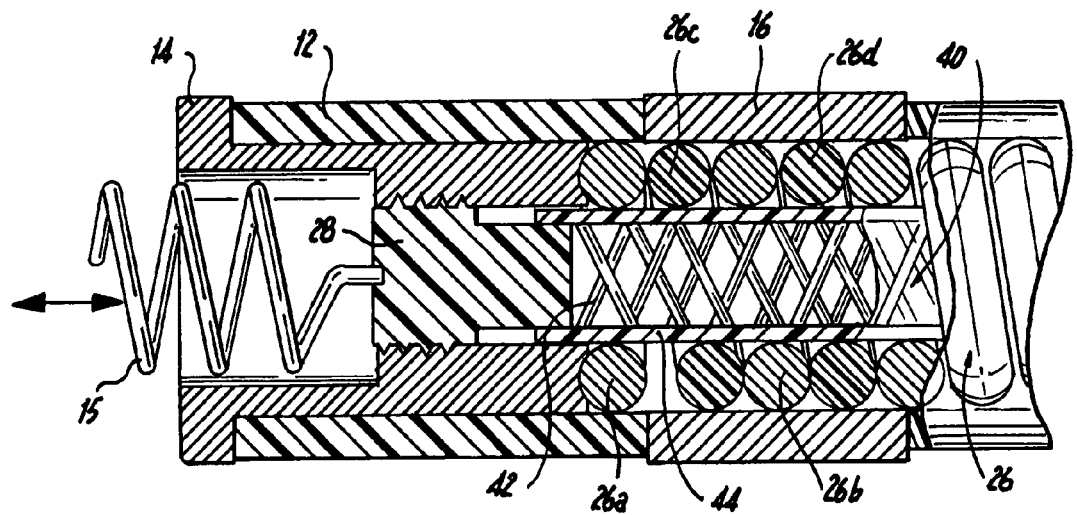
FIG. 7 is a cross-sectional view of the distal end portion of the cardiac lead of the subject invention, similar to FIG. 3, wherein the torque-transmitting member comprises an electrically inactive braid covered or otherwise coated by a polymer tube and illustrating the engagement of the torque-transmitting member and the helical fixation screw.
Figure 8:
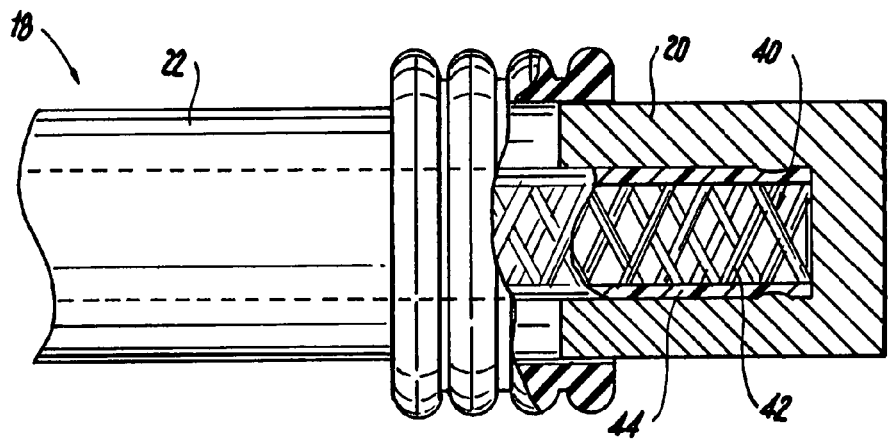
FIG. 8 is a cross-sectional view of the proximal end portion of the cardiac lead of the subject invention, similar to FIG. 4, wherein the torque-transmitting member comprises an electrically inactive braid covered or otherwise coated by a polymer tube, and illustrating the engagement of the torque-transmitting member and the rotatable pin portion of the proximal connector.

Referring now to FIGS. 7 and 8, there is illustrated another embodiment of the torque-transmitting member of the subject invention that is designated generally by reference numeral 40. The torque-transmitting member or torquing tube 40 is substantially similar to torquing tube 30 of FIGS. 3 and 4, except that it includes an electrically inactive braid 42 that is embedded or molded into or otherwise covered by polymer tubing 44, which is preferably heat shrunk (e.g., heat reflow process) over the braid 42. As shown in FIG. 8, the proximal end of the torque transmitting mechanism 40 is operatively connected to the rotateable pin portion 20 of the connector 18 (or to another rotateable portion of the connector), while the distal end of mechanism 40 is operatively connected to the threaded plug 28, carrying fixation helix 15.

In accordance with the subject invention, torque-transmitting member 30, 40 is coaxially arranged within the lumen of electrically active multifilar conductor coil 26 of pacing lead 10. The polymer tubing 34, 44 covering the radially inner coil/braid 32/42 reduce friction between the torque-transmitting mechanism 30, 40 and the radially outer multifilar conductor coil 26 during fixation of screw 15. In addition, the coaxial construction of lead 10 allows for a relatively low profile lead body design (e.g., a lead body size of about 4.8 F), which is extremely advantageous.

While the apparatus and methods of subject invention have been shown and described with reference to preferred embodiments, those skilled in the art will readily appreciate that changes and/or modifications may be made thereto without departing from the spirit and cope of the subject invention. For example, the low profile cardiac pacing lead of the subject invention can be configured as a unipolar pacing lead or the lead body can have a preformed shape, such as for example, a J-shaped configuration.

What is claimed is:

1. A cardiac lead comprising:
   a) an elongated lead body having opposed proximal and distal end portions and having an interior lumen extending therethrough;
   b) a rotatable fixation element operatively associated with the distal end portion of the lead body;
   c) a conductor coil extending through the interior lumen of the lead body wherein the conductor coil is a multifilar coil having interposed electrically active and inactive filars;
   d) a tubular torque transmitting member extending through the interior lumen of the lead body, coaxially arranged within the conductor coil, and having opposed proximal and distal ends, the proximal end of the tubular torque transmitting member connected to a rotatable actuator operatively and integrally connected with the proximal end portion of the lead body, such that rotation of the rotatable actuator causes corresponding rotation of the tubular torque transmitting member with respect to the elongated lead body and the conductor coil wherein the tubular torque transmitting member includes an electrically inactive helically wound coil; and
   e) a threaded plug associated with the distal end portion of the lead body, carrying the rotatable fixation element and operatively connected to the distal end of the tubular torque transmitting member, such that rotation of the tubular torque transmitting member by the rotatable actuator causes corresponding rotation of the fixation element.

2. A cardiac lead as recited in claim 1, wherein the tubular torque transmitting member helically wound coil is covered by a polymer tube.

3. A cardiac lead as recited in claim 2, wherein the polymer tube is heat shrunk over the helically wound coil.

4. A cardiac lead as recited in claim 1, wherein the torque-transmitting member includes a braided structure.

5. A cardiac lead as recited in claim 4, wherein a polymer tube covers the braided structure.

6. A cardiac lead as recited in claim 5, wherein the polymer tube is heat shrunk over the braided structure.

7. A cardiac lead as recited in claim 4, wherein the braided structure is embedded in a polymer tube.

8. A cardiac lead as recited in claim 1, wherein the rotatable fixation element is a helical fixation screw.

9. A cardiac lead as recited in claim 1, wherein the rotatable actuator is part of a connector associated with the proximal end portion of the lead body.

10. A cardiac lead as recited in claim 9, further comprising an electrode assembly operatively associated with the distal end portion of the lead body, wherein the electrode assembly is operatively connected to the connector by way of the conductor coil extending through the interior lumen of the lead body.

11. A cardiac lead as recited in claim 10, wherein the electrode assembly is a bipolar pacing assembly having a distal tip electrode and a proximal ring electrode.

12. An active fixation cardiac lead comprising:
    a) an elongated lead body having opposed proximal and distal end portions and having an interior lumen extending therethrough;
    b) an electrode assembly associated with the distal end portion of the lead body;
    c) a connector assembly associated with the proximal end portion of the lead body and including a rotatable actuator;
    d) a conductor coil extending through the interior lumen of the lead body between the electrode assembly and the connector assembly;
    e) a rotatable fixation member associated with the distal end portion of the lead body and carried by a threaded plug; and
    f) an electrically inactive tubular torque transmitting member extending coaxially through the conductor coil, wherein a distal end of the torque-transmitting member is operatively connected to the threaded plug and a proximal end of the torque-transmitting member is operatively connected to the rotatable actuator of the connector assembly operatively and integrally connected with the proximal end portion of the lead body, wherein rotation of the rotatable actuator causes corresponding rotation of the tubular torque transmitting member and the threaded plug carrying the fixation member, with respect to the elongated lead body and the conductor coil wherein only a portion of an outer surface of the tubular torque transmitting member is covered by an electric insulation layer.

13. An active fixation cardiac lead as recited in claim 12, wherein the electric insulation layer consists of a polymer tube.

14. An active fixation cardiac lead as recited in claim 13, wherein the polymer tube is heat shrunk over the helically wound coil.

15. An active fixation cardiac lead as recited in claim 12, wherein the torque-transmitting member includes a braided structure.

16. An active fixation cardiac lead as recited in claim 15, wherein a polymer tube covers the braided structure.

17. An active fixation cardiac lead as recited in claim 16, wherein the polymer tube is heat shrunk over the braided structure.

18. An active fixation cardiac lead as recited in claim 17, wherein the braided structure is embedded in a polymer tube.

19. An active fixation cardiac lead as recited in claim 12, wherein the rotatable fixation element is a helical fixation screw.

20. An active fixation cardiac lead as recited in claim 12, wherein the electrode assembly is a bipolar pacing assembly having a distal tip electrode and a proximal ring electrode.

* * * * *